United States Patent [19]
Latimer

[11] Patent Number: 5,359,898
[45] Date of Patent: Nov. 1, 1994

[54] HYDROGEN DAMAGE CONFIRMATION WITH EMATS

[75] Inventor: Paul J. Latimer, Lynchburg, Va.

[73] Assignee: The Babcock & Wilcox Company, New Orleans, La.

[21] Appl. No.: 891,595

[22] Filed: Jun. 1, 1992

Related U.S. Application Data

[63] Continuation-in-part of Ser. No. 710,271, Jun. 4, 1991, Pat. No. 5,243,862.

[51] Int. Cl.$^5$ .................. G01N 29/08; G01N 29/26
[52] U.S. Cl. ........................... 73/600; 73/622; 73/634; 73/643
[58] Field of Search ............. 73/599, 600, 634, 643, 73/592, 596, 620, 622, 637, 638

[56] References Cited

U.S. PATENT DOCUMENTS

| | | | |
|---|---|---|---|
| 3,850,028 | 11/1974 | Thompson et al. | 73/638 |
| 4,127,035 | 11/1978 | Vasile | 73/629 |
| 4,289,030 | 9/1981 | Alers et al. | 73/637 |
| 4,307,612 | 12/1981 | Eisley et al. | 73/613 |
| 4,320,661 | 3/1982 | Peterson et al. | 73/643 |
| 4,593,568 | 4/1986 | Telford et al. | 73/623 |
| 4,685,334 | 8/1987 | Latimer | 73/599 |
| 4,890,496 | 1/1990 | Birring et al. | 73/599 |
| 5,085,082 | 2/1992 | Cantor et al. | 73/622 |

OTHER PUBLICATIONS

Latimer, P. J., D. M. Stevens, and T. P. Sherlock, "A NDE Method for Hydrogen Damage Detection in Boiler Tubes", Proceedings of the EPRI Conference on Life Extension and Assessment of Fossil Plants, Washington, D.C., Jun. 2-4, 1986, EPRI C5-5208, pp. 1061-1076.

Latimer, P. J. and H. L. Whaley, "Electromagnetic Transducers for Generation and Detection of Ultrasonic Waves", *Acousto-Ultrasonics*, Edited by John C. Duke Jr., Plenum Publishing Corporation, 1988 (Presented at the Symposium on Acousto-Ultrasonics, Jul. 12-15, 1987, Virginia Polytechnic and State University, Blacksburg, Va.

Birring, A. S., D. G. Alcazar, J. J. Hanley and S. M. Gehl, "Ultrasonic Assessment of Creep and Hydrogen Damage in Fossil Plant Components", *Proceedings of the Second EPRI Fossil Plant Inspection Conference*, Nov. 29-Dec. 1, 1988 San Antonio, Tex.

Birring, A. S., D. G. Alcazar, J. J. Hanley, and S. Gehl, "Ultrasonic Detection of Hydrogen Damage", *Materials Evaluation* 47 Mar. 1989 pp. 345-350.

Sloat, Kim A., and Doug Jacks, "Inspection for Hydrogen Damage in Waterwall Tubes Using Ultrasonic Techniques," Proceedings of the EPRI Conference on Failures and Inspections of Fossil-Fired Boiler Tubes, EPRI CS-3272, Bal Harbor, Florida, Apr., 1983.

B. W. Maxfield, A. Kuramoto, and J. K. Hulbert, "Evaluating EMAT Designs for Selected Applications", *Materials Evaluation*, 45 Oct. 1987 pp. 1166-1183.

*Primary Examiner*—Hezron E. Williams
*Assistant Examiner*—Rose M. Finley
*Attorney, Agent, or Firm*—Daniel S. Kalka; Robert J. Edwards

[57] ABSTRACT

A method and apparatus for use in confirming hydrogen damage in a boiler tube comprises a pair of electromagnetic acoustic transducer coils which are mounted for movement toward and away from each other. An electromagnet produces pulses that generate acoustic beams across a chord and within the wall thickness of the boiler tube. For adapting to boiler tubes of different outside diameters, the transducers coils are mounted on a resilient member so that the coils can be pressed against the outer surface of coils having a variety of outside diameters. The angle of the acoustic beam between the coils must also be adjusted, however, and this is done by changing the frequency of energy applied to the coils.

11 Claims, 4 Drawing Sheets

HYDROGEN DAMAGE CONFIRMATION WITH EMATS

This application is a continuation-in-part of application Ser. No. 07/710,271 filed Jun. 4, 1991, now U.S. Pat. No. 5,243,862.

BACKGROUND OF THE INVENTION

1. Field of the Invention

The present invention relates in general to the ultrasonic detection of hydrogen damage in boiler tubes, and in particular to a new and useful method and apparatus for confirming the presence of hydrogen damage, using movably mounted electromagnetic transducers (EMATs) which can be pressed closely against and at an accurate spacing or lift-off from the outer surface of a boiler tube having a range of different outside diameters (ODs).

2. Description of the Related Art

Starting in 1983, The Babcock & Wilcox Company developed a successful technique for the detection of hydrogen damage in fossil fired boilers. The technique was based on the attenuation of conventional ultrasonic waves in damaged sections of boiler tubes. Since that time, over 50 units have been inspected with excellent results. In many cases, a full inspection of the waterwall was requested. In one medium size unit, this required over 250 gallons of couplant and scanning over 10 miles of tubing and 1100 welds. In order to make this task easier, electromagnetic acoustic transducers (EMATs) were used to eliminate the need for couplant and increase the scanning speed. U.S. Pat. No. 4,685,334 discloses both conventional and EMAT techniques for detecting hydrogen damage in boiler tubes.

A new technique for hydrogen damage confirmation has been developed recently. A confirmation technique was needed since under certain conditions, such as extreme inside diameter (ID) pitting, both the conventional and EMAT techniques produced indications that could not be distinguished from actual hydrogen damage. The confirmation technique was based upon refraction of shear waves across a chord in a boiler tube. This technique was field tested using conventional ultrasonics in a unit which had extreme outer diameter (OD) erosion on a large section of the waterwall. It was clearly demonstrated that the chordal technique was superior under those adverse conditions. In addition a tube was removed, sectioned, and etched with nital in the field. Hydrogen damage was confirmed at the exact location indicated by the chordal technique.

There are some disadvantages to the chordal technique using conventional ultrasonics. A different beam angle must be used for each combination of tube OD and wall thickness. This requires a pair of special wedges for each particular tube-wall combination.

A comprehensive description of the structure and operation of EMATs, can be found in "Evaluating EMAT Designs for Selected Applications", B. W. Maxfield, et al *Materials Evaluation*, 45, October, 1987.

Additional information on non-destructive ultrasonic and electromagnetic acoustic devices and testing can be found in U.S. Pat. Nos. 4,127,035; 4,307,612; 4,320,661; and 4,593,568.

SUMMARY OF THE INVENTION

The present invention comprises an apparatus for confirmation of hydrogen damage which utilizes a pair of spaced apart and movably mounted EMAT coils which are held on a flexible support so that they can be pressed against the OD of a boiler tube to form a close yet accurate and reproducible lift-off or spacing between the transducer coils and the tube surface, the EMATs being operated in a bulk angle-beam SH (shear horizontal) wave mode having an adjustable angle.

According to the invention, boiler tubes having different ODs can be serviced by the same apparatus. The EMAT coils are used in either a pitch-catch or transmit-receive mode.

Advantages of the invention include the fact that no couplant is required for EMATs. This increases the speed of the confirmation. The need for special wedges used with piezoelectric acoustic sensors to adapt to different tube diameter and wall thicknesses, is also eliminated. The present invention provides a universal apparatus or search unit utilizing the SH shear wave EMATs. It is also very easy to interpret dB dropoff in attenuation so that minimal training is needed for field technicians. The apparatus and method of the present invention can be integrated into an automated boiler inspection scheme since no couplant is required. Although the invention is contemplated primarily for use in confirming hydrogen damage, it may also be utilized to detect hydrogen damage in the first incidence. This may replace multiple techniques currently used to first detect and then confirm hydrogen damage.

Accordingly, an object of the present invention is to provide an apparatus for use in confirming hydrogen damage in the wall of a boiler tube having an outside diameter, comprising: a pair of spaced apart electromagnetic acoustic transducer coils; first mounting means connected to the coils for changing a spacing between the coils; second mounting means connected to the coils for holding the coils in a chordal orientation so that each coil can face a boiler tube outside diameter around a circumference of the boiler tube corresponding to the spacing between the coils; beam angle control means operatively connected to the coils for adjusting a beam angle of an acoustic beam between the coils so that the acoustic beam passes along a chord of the boiler tube within a wall thickness of the boiler tube; and magnetic pulser/receiver means operatively connected to the coils for generating and receiving acoustic beams between the coils, the received beam containing information useful in confirming the existence of hydrogen damage in the boiler tube wall thickness.

A further object of the present invention is to provide a method for use in confirming the existence of hydrogen damage in the wall of a boiler tube having an outside diameter, comprising: moving a pair of electromagnetic acoustic transducer coils to a selected spacing from each other; applying the coils against the outside diameter of a boiler tube, the coils being spaced around the circumference of the tube depending on the selected space between the coils; controlling a beam angle of an acoustic beam between the coils so that the beam angle passes along a chord of the boiler tube within a wall thickness of the boiler tube; applying electric current pulses to the coils with the coils located in a pulsed magnetic field for generating the acoustic beam; and receiving and measuring the acoustic beam at one of the coils, the measurement of the acoustic beam providing information which can be used to confirm the existence of hydrogen damage in the wall thickness of the boiler tube.

A further object of the present invention is to provide an apparatus and method of confirming hydrogen damage in boiler tubes which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
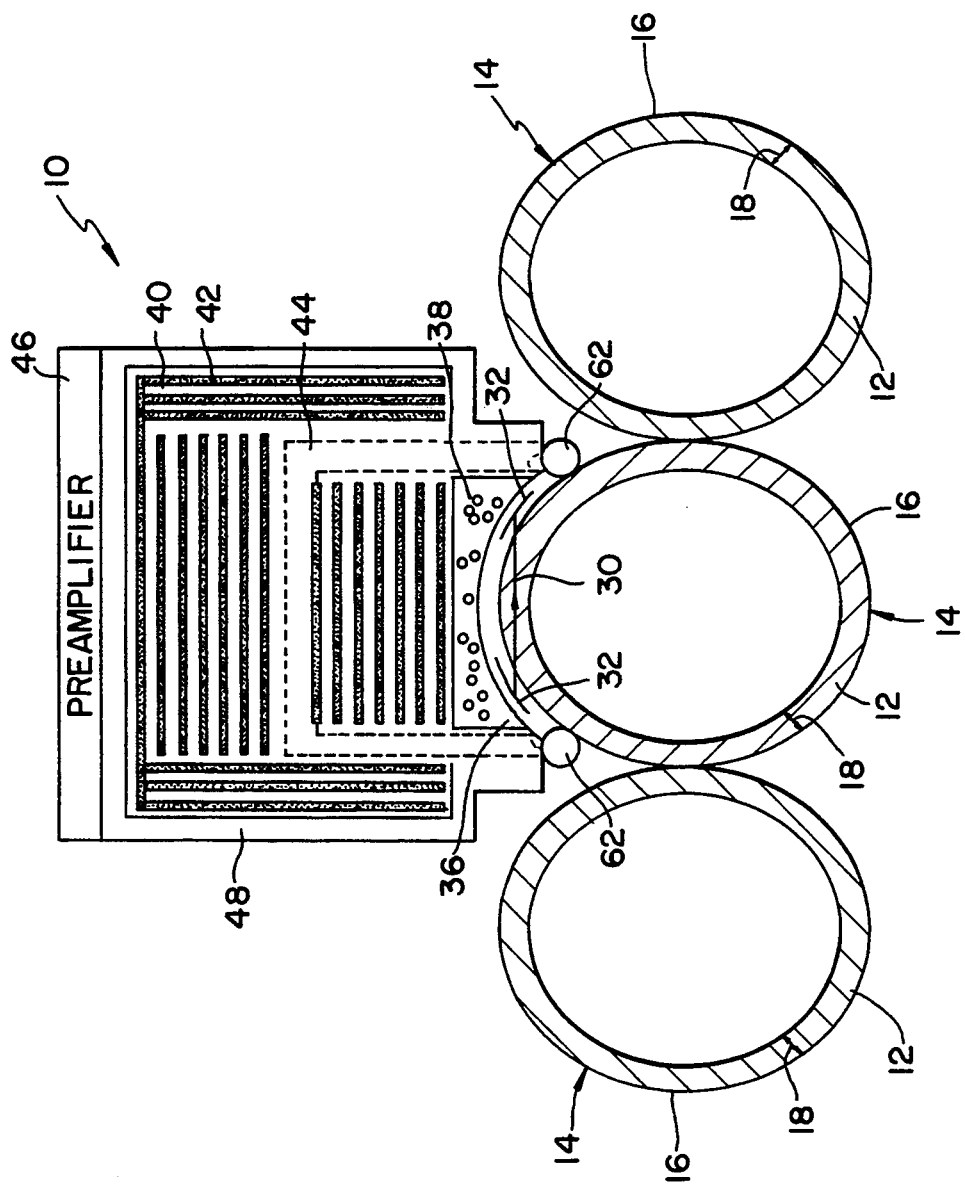
FIG. 1 is a schematic top plan view of an EMAT apparatus used to confirm or detect hydrogen damage in the walls of boiler tubes according to the invention.
Figure 2:
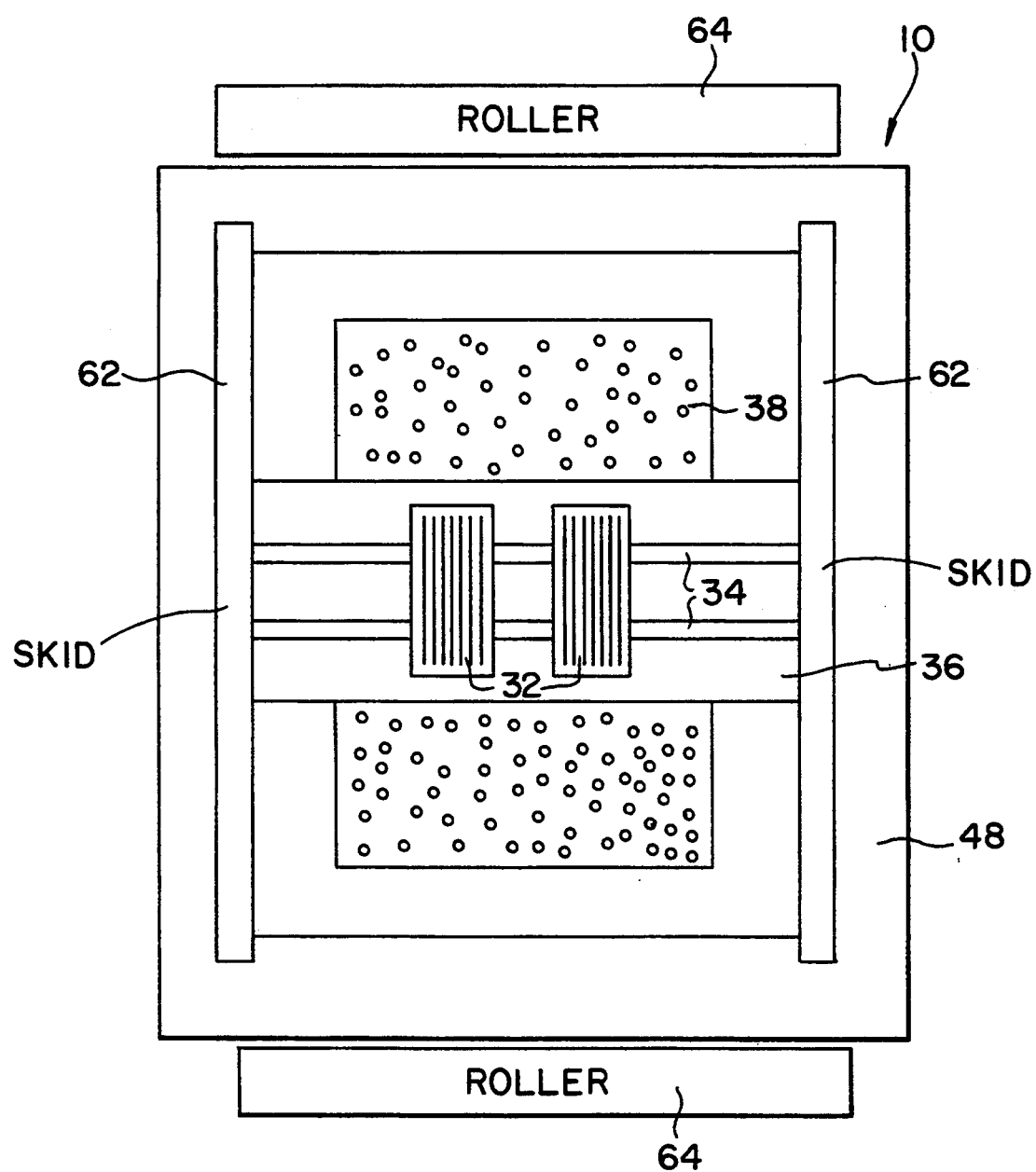
FIG. 2 is a front elevational view of the apparatus illustrated in FIG. 1.

Referring to the drawings in particular, the invention embodied in FIG. 1 and FIG. 2 comprises an apparatus and method for use in confirming the existence of hydrogen damage in the walls (12) of boiler tubes generally designated (14) having particular outside diameters OD (16) and particular wall thicknesses (18).

Figure 3:
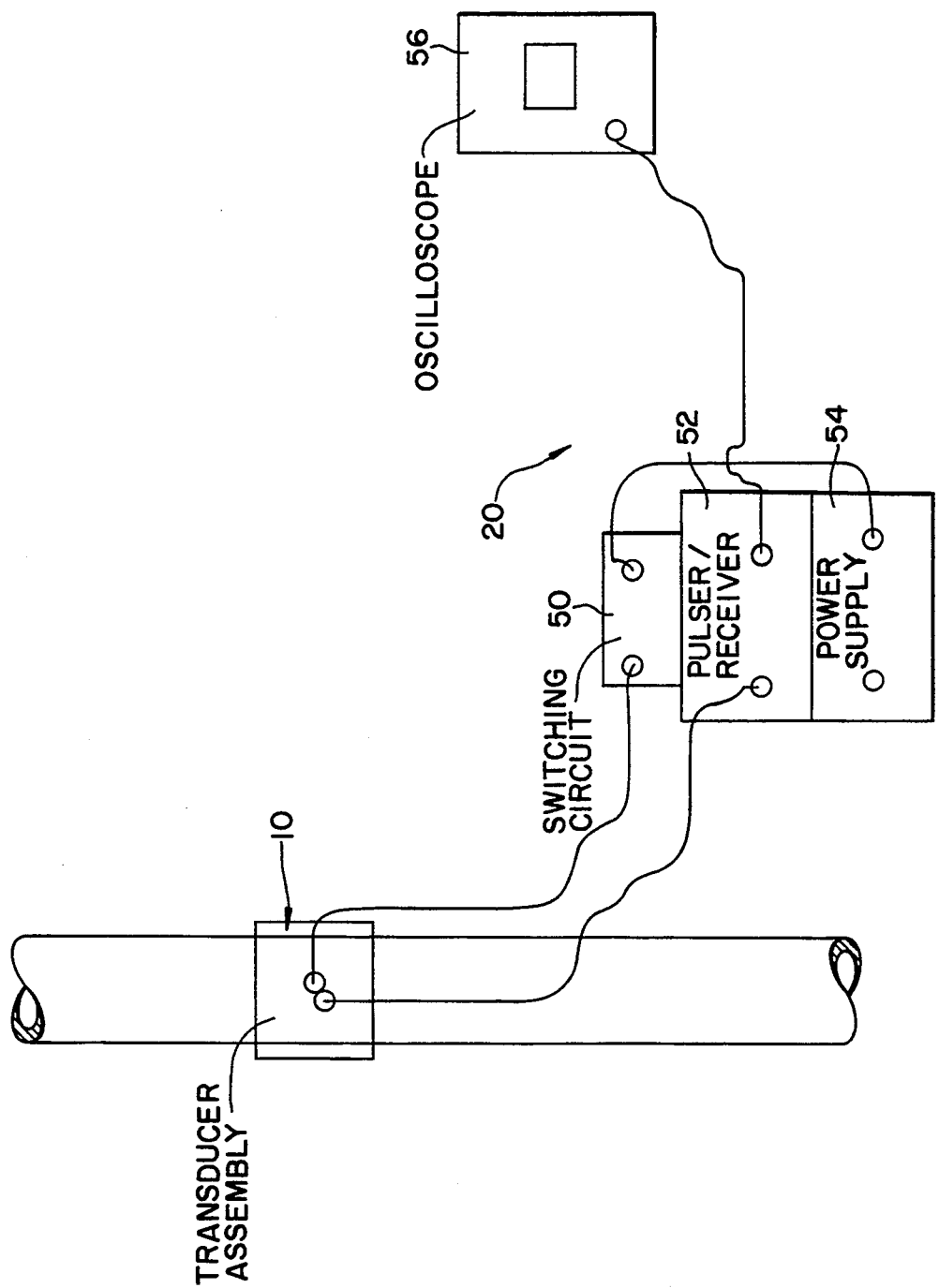
FIG. 3 is a schematic representation of equipment connected to the EMAT apparatus, in accordance with the present invention.

The apparatus, which includes a transducer assembly generally designated (10) and additional powering and interpretation equipment generally designated (20) and illustrated in FIG. 3, generates and receives an acoustic beam (30) which passes along a chord in the tube wall (12), and is directed to pass within the wall thickness. By interpreting the attenuation dropoff in the signal (measured in dB) even a technician with little training can distinguish between hydrogen damage and other types of damage to the tube wall.

An important feature of the present invention is that the transducer assembly can adapt to different boiler tube ODs. This is done by mounting a pair of EMAT coils (32) so that they can be spaced from each other by different selected amounts and further by providing equipment that can adjust the shear angle, and in particular the shear horizontal (SH) angle of the EMAT beam (30) so that it remains within the wall thickness of the tube. It is also advantageous to mount the transducer coils (32) in a flexible manner so that they can be closely pressed against the OD of boiler tubes having different diameters, thus reducing and accurately defining the lift-off characteristic, that is distance between the coil faces and the outer surface of the tube.

As best shown in FIG. 2, first mounting means for adjusting the distance between the pair of coils (32), comprises a pair of slots (34) defined within a flexible non-magnetic spring strip (36). Grooves, for example, dove tail grooves, can be provided on the rear surfaces of coils (32) and the grooves (34) can also be dove tail to slidably receive the coils.

Any other mechanism for slidably mounting the coils (32) so that their spacing can be changed, can be utilized in accordance with the present invention.

The flexible mounting of the coils is achieved by using second mounting means in the form of a flexible resilient backing member (38), made for example of resilient foam, on which the flexible non-magnetic spring strip (36) is mounted, for example by adhesive. The flexibility of strip (36) and resiliency of mounting member (38), allows the second mounting means to hold the coils in a selected chordal orientation so that the coils can face and be pressed closely against the outside diameter of the boiler tube.

The transducer assembly (10) further includes an electromagnet (40) having magnetic windings (42) which are engaged onto a laminated magnetic core (44) having a substantially U-shaped configuration. The resilient mounting member (38) can be positioned with the arms of the core (44) to advantageously and properly position the transducer coils (32) with respect to the magnetic field generated by magnetic (40). Magnet (40) is held within an aluminum or other suitable provided fixture (48).

A matching network and preamplifier (46) is placed on the back of magnet (40) for matching the impedance increasing the signal level, and allowing longer cables to be used.

As best shown in FIG. 3, the driving equipment (20) includes a switching circuit (50) for pulsing the magnet and providing the timing signals, and EMAT pulser/receiver (52) for applying and receiving the signals from the transducers, and a power supply (54). Pulser/receiver (52) is connected to any appropriate monitoring equipment such as a PC or an oscilloscope shown schematically at (56).

Figure 6:
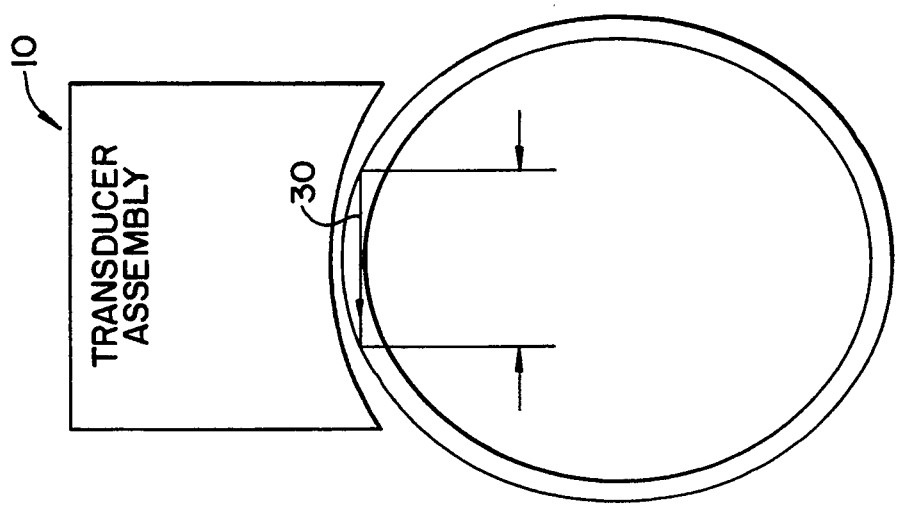
FIG. 6 is a view similar to FIG. 4, showing use of the invention on a large OD boiler tube.
Figure 5:
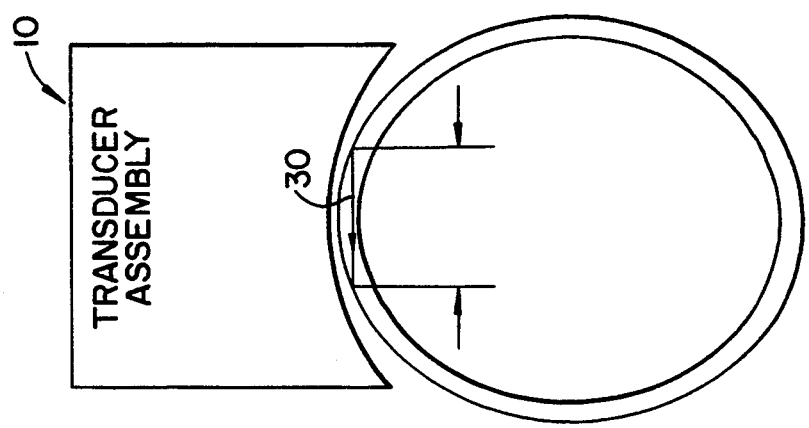
FIG. 5 is a view similar to FIG. 4, showing use of the invention on a medium size OD boiler tube.
Figure 4:
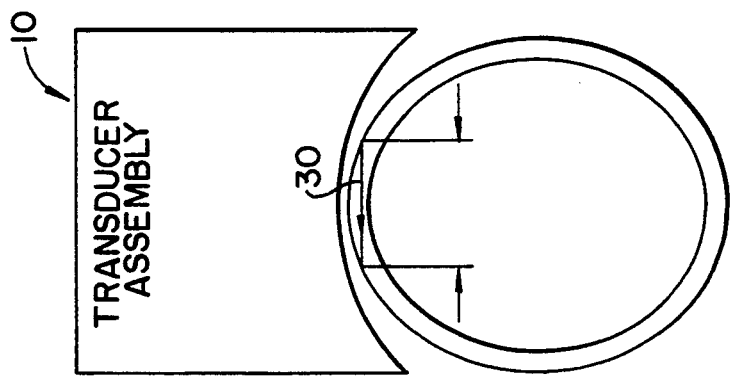
FIG. 4 is a schematic top plan view of the apparatus of the present invention used in conjunction with a small OD boiler tube.

The beam angle is controlled by the frequency of the EMAT pulser/receiver. The equipment (20) includes, for example, means for adjusting the angle of beam (30), so that it stays within the wall thickness of the tube. As illustrated in FIGS. 4, 5 and 6, it is important to adjust both the separation between coils and the acoustic beam angle, in order to achieve proper chordal positioning of the beam (30).

In FIG. 4, for example, a boiler tube having an OD of 2 inches has hydrogen damage confirmed using acoustic beam (30) which is 13/16 inches long within the chord of the tube wall thickness of 0.180 inches.

In FIG. 5, an OD of 2.5 inches is serviced by a beam 30 which is 15/16 inches long, the tube wall being 0.200 inches.

In FIG. 6, a 3.0 inch OD tube having a wall thickness of 0.25 inches utilizes an acoustic beam (30) of 1 and 3/16 inches in length. The change in separation of the transducer coils which achieves the beams in different lengths must be accompanied by angle adjustment for the beams emanating from and being received by the transducer coils.

The wave mode for the coils (32) is chosen to be SH shear waves because the beam angle can be adjusted by changing the frequency. This follows from the relation:

$$\sin \theta = V_s/(2Df)$$

where:

$V_s$ = bulk wave velocity;

D = separation between adjacent conductors on the EMAT; and
f = frequency

There are two method of generating Sit shear waves. One method uses a periodic array of permanent magnets whose thickness is equal to one half the wavelength of the ultrasound. This method is limited to frequencies of one MHz or less because the brittle ceramic magnets are difficult to machine thin enough for higher frequencies. The other method uses the magnetostrictive effect to generate ultrasonic waves. This method uses a meander coil with the conductors parallel to the magnetic field. This is in contrast to the generation of SV shear waves where the conductors are perpendicular to the field.

Since higher frequencies are required to demonstrate significant attenuation in hydrogen damaged material, the magnetostrictive technique is used for hydrogen damage confirmation. The pulsed magnet with the laminated core is used to avoid magnetic drag associated with other types of magnets. FIG. 1 illustrates that the same core can be used on typical boiler tubes. By using a fixture with adjustable skids or rollers (62, 64) (see FIGS. 1 and 2), a variable lift-off can be adjusted to provide sufficient field strength near the EMATs.

The EMATs illustrated are used in a pitch-catch mode. This is required by the nature of the chordal technique. In the conventional technique, the beam is refracted across a chord of the tube wall as it propagates from the wedge material to the steel comprising the boiler tube. With SH shear wave EMATs, the appropriate beam angle is chosen by adjusting the frequency as previously described. FIG. 2 shows a facing view of the sensor assembly. The coils (32) are actually flexible printed circuits covered by a 5 mil thick strip of polyethylene tape. The tape acts as a tough wear surface for the EMAT while scanning a boiler tube. The flexible printed circuit is backed by the resilient foam that forces the EMAT to conform to any contour tube while the tape maintains constant lift-off. The distance between entrance-exit points is determined by the relation:

$$L = 2r \cos \theta$$

where:

L = distance between entrance-exit points;
r = outside radius of the tube; and
$\theta$ = beam angle of the ultrasound in steel.

The position of the entrance-exit points can be adjusted by sliding the EMATs along the slots (34) in the flexible nonmagnetic strip (36). Once the correct entrance-exit points have been chosen the EMATs are locked in position by screws or clips (not shown). The flexible strip conforms to the curvature of the tube allowing the entrance-exit points to be changed without changing the 5 mil lift-off between the EMAT coil and tube surface.

The use of matching circuits and preamplifiers as shown in FIG. 3 allows cable lengths of more than 100 feet between the instrumentation and sensor leads. This would allow the power supply to be placed on the floor of the boiler or in some instances outside of the boiler.

While a specific embodiment of the invention has been shown and described in detail to illustrate the application of the principles of the invention, will be understood that the invention may be embodied otherwise without departing from such principles.

What is claimed is:

1. An apparatus for detecting hydrogen damage in a boiler tube, comprising:
    a pair of spaced apart electromagnetic acoustic transducer coils;
    first mounting means connected to the coils for changing a spacing between the coils;
    second mounting means connected to the coils for holding the coils in a spaced chordal orientation so that each coil faces an outside surface of a boiler tube;
    beam angle control means operatively connected to the coils for adjusting a beam angle of an acoustic beam between the coils so that the acoustic beam passes along a chord of the boiler tube within a wall thickness of the boiler tube;
    electromagnetic pulser/receiver means operatively connected to the coils for generating and receiving acoustic beams between the coils; and
    means for monitoring a received acoustic beam, an attenuation of the received acoustic beam being indicative of hydrogen damage in the boiler tube.

2. An apparatus according to claim 1, wherein said second mounting means comprises a resilient member and a non-magnetic spring strip attached to the resilient member and carrying the pair of spaced apart coils, the non-magnetic spring strip being flexible into a curved shaped corresponding to an outer circumference of a boiler tube.

3. An apparatus according to claim 2, wherein said first mounting means comprises at least one slot along the non-magnetic spring strip for slidably receiving each of the coils.

4. An apparatus according to claim 2, wherein each coil comprises a flexible printed circuit, and a synthetic tape strip over each coil for maintaining a constant lift-off between each coil and the outside surface of the boiler tube.

5. An apparatus according to claim 1, wherein each coil comprises a flexible printed circuit, and a synthetic tape strip over each coil for maintaining a constant lift-off between each coil and the outside surface of the boiler tube.

6. An apparatus according to claim 1, wherein said electromagnetic pulser/receiving means comprises an electromagnet having a laminated core, and said beam angle control means comprises means for changing a frequency of energy applied to the coils.

7. An apparatus according to claim 6, wherein the laminated core of the electromagnet is oriented with respect to the coils so that the coils produce a shear horizontal wave acoustic beam in the chord of a boiler tube.

8. A method for detecting hydrogen damage in a boiler tube, comprising the steps of:
    moving a pair of electromagnetic acoustic transducer coils to a selected spacing from each other;
    applying the coils against an outside surface of a boiler tube, the coils being spaced around the boiler tube at a selected space between the coils;
    controlling a beam angle of an acoustic beam between the coils so that the beam passes along a chord of the boiler tube within a wall thickness of the boiler tube;
    applying electric current pulses to the coils for generating the acoustic beam;

receiving the acoustic beam at one of the coils; and measuring an attenuation of the received acoustic beam to detect hydrogen damage in the boiler tube.

9. A method according to claim 8, including the step of changing the angle of the acoustic beam by changing the frequency of energy applied to the coils.

10. A method according to claim 9, including the step of generating the electric current pulses by applying electric current pulses to the electromagnetic acoustic transducer coils in a pulsed magnetic field in a direction to produce a shear horizontal wave along the acoustic beam.

11. A method according to claim 8, including the steps of adjusting a spacing between the coils by movably mounting the coils on a flexible spring strip of non-magnetic material, orienting the coils against the surface of a boiler tube by mounting the strip on a resilient member and pressing the resilient member toward the boiler tube.

* * * * *